United States Patent
Alenfall et al.

(10) Patent No.: US 9,687,513 B2
(45) Date of Patent: Jun. 27, 2017

(54) **METHODS OF TREATING ANEMIA AND INCREASING THE ABSORPTION OF NON-HEME IRON BY ADMINISTRATION OF *LACTOBACILLUS PLANTARUM***

(75) Inventors: Jan Alenfall, Lomma (SE); Anna Berggren, Flyinge (SE)

(73) Assignee: Probi AB, Lund (SE)

( * ) Notice: Subject to any disclaimer, the term of this patent is extended or adjusted under 35 U.S.C. 154(b) by 1450 days.

(21) Appl. No.: 11/922,954

(22) PCT Filed: Jul. 4, 2006

(86) PCT No.: PCT/SE2006/000846
§ 371 (c)(1),
(2), (4) Date: Feb. 29, 2008

(87) PCT Pub. No.: WO2007/004966
PCT Pub. Date: Jan. 11, 2007

(65) Prior Publication Data
US 2009/0098190 A1    Apr. 16, 2009

(30) Foreign Application Priority Data
Jul. 5, 2005 (SE) .................................... 0501556

(51) Int. Cl.
| | | |
|---|---|---|
| A61K 35/00 | (2006.01) | |
| A61K 35/747 | (2015.01) | |
| A21D 2/02 | (2006.01) | |
| A21D 8/04 | (2006.01) | |
| A23C 9/123 | (2006.01) | |
| C12R 1/25 | (2006.01) | |
| A61K 33/06 | (2006.01) | |
| A61K 33/26 | (2006.01) | |
| A61K 33/30 | (2006.01) | |
| A23L 7/143 | (2016.01) | |
| A23L 33/135 | (2016.01) | |

(52) U.S. Cl.
CPC .............. *A61K 35/747* (2013.01); *A21D 2/02* (2013.01); *A21D 8/045* (2013.01); *A23C 9/1234* (2013.01); *A23L 7/143* (2016.08); *A23L 33/135* (2016.08); *A61K 33/06* (2013.01); *A61K 33/26* (2013.01); *A61K 33/30* (2013.01); *C12R 1/25* (2013.01); *A23Y 2220/00* (2013.01)

(58) Field of Classification Search
None
See application file for complete search history.

(56) References Cited

U.S. PATENT DOCUMENTS

| | | | |
|---|---|---|---|
| 5,591,428 A | 1/1997 | Bengmark et al. | |
| 6,159,465 A * | 12/2000 | Adlerberth et al. | 424/93.45 |
| 7,311,932 B1 * | 12/2007 | Berggren et al. | 426/61 |
| 7,507,572 B2 * | 3/2009 | Molin et al. | 435/252.9 |
| 7,807,440 B2 * | 10/2010 | Molin et al. | 435/252.1 |
| 2002/0127211 A1 * | 9/2002 | Brassart et al. | 424/93.45 |

FOREIGN PATENT DOCUMENTS

| | | |
|---|---|---|
| EP | 1003532 B1 | 7/2001 |
| JP | 6-508516 | 9/1994 |
| JP | 70 53391 A | 2/1995 |
| JP | 2002-507997 | 3/2002 |
| JP | 2002-540807 | 12/2002 |
| WO | WO 9902170 A1 | 1/1999 |
| WO | WO 0060950 A1 | 10/2000 |
| WO | WO-00/0070972 A1 | 11/2000 |
| WO | WO 01/15715 | 3/2001 |
| WO | WO 2004/087893 | 10/2004 |

OTHER PUBLICATIONS

Klarin (http://www.controlled-trials.com/isrctn/pf/00472141) ( accesses Nov. 8, 2010.*
Naruszewicz et al., Am J Clin Nutr 2002;76:1249-55.*
Lamanca et al., International Journal of Sport Nutrition, 1992, 2, 376-385.*
Nielson et al. J. Agric. Food Chem. 1988, 36, 1211-1216.*
English translation of Chinese Office Action dated Aug. 6, 2010 in Chinese counterpart Application No. 200680031271.7.
*Influence of Lactic Acid Fermentation on Nutritive Value of Some Cereals*, Food Science, Dec. 31, 1988, pp. 7-9 (in Chinese with English translation).
Keiko Shirai et al., "Ability of some strains of lactic acid bacteria to degrade phytic acid", Letters in Applied Microbiology, 1994, vol. 19, pp. 366-369.
Anna Reale et al., "Phytate Degradation by Lactic Acid Bacteria and Yeasts during the Wholemeal Dough Fermentation: a 31P NMR Study", J. Agric. Food Chem. 2004, vol. 52, pp. 6300-6305.
G. Önning et al., Influence of a drink containing different antioxidants and Lactobacillus plantarum 299v on plasma total antioxidant capacity, selenium status and faecal microbial flora, International Journal of Food Sciences and Nutrition, Jul. 2003, vol. 54, No. 4, sidor 281-289.
I.M. Marklinder et al., "Degradation of phytate by using varied sources of phytases in an oat-based nutrient solution fermented by Lactobacillus plantarum strain 299V", Food Microbiology, 1995, vol. 12, pp. 487-495.
Jesus M. Porres, et al., "Effect of Natural and Controlled Fermentation on Chemical Composition and Nutrient Dialyzability from Beans (*Phaseolus vulgaris* L.)", J. Agric. Food Chem. 2003, vol. 51, pp. 5144-5149.
Taishi Oda et al., "Effect of Lactobacillus acidophilus on Iron Bioavalability in Rats", Journal of nutritional science and viraminology, 1994, vol. 40, pp. 613-616.
M. Zamudia et al., "Lactobacillus plantarum phytase activity is due to non-specific acid phosphatase", Letters in Applied Microbiology, 2001, vol. 32, pp. 181-184.

(Continued)

Primary Examiner — Irene Marx
(74) *Attorney, Agent, or Firm* — McCarter & English, LLP; Steven G. Davis; Yu Lu

(57) ABSTRACT

The present invention relates to the use of at least one strain of *Lactobacillus plantarum* chosen from the group comprising *Lactobacillus plantarum* 299, DSM 6595, *Lactobacillus plantarum* '299v, DSM 9843, *Lactobacillus plantarum* HEAL 9, DSM 15312, *Lactobacillus plantarum* HEAL 19, DSM 15313, Lactobacillus plantarum HEAL 99, DSM 15316, and a part thereof, for the preparation of a composition for increasing the absorption of at least one kind of metal/metal ion in a mammal, preferably a human.

13 Claims, No Drawings

(56) References Cited

OTHER PUBLICATIONS

English translation of Office Action mailed on Apr. 3, 2012, in corresponding Japanese Patent Application No. 2008-519228.
R. J. Kennedy et al., *Probiotic Therapy Fails to Improve Gut Permeability in a Hapten Model of Colitis*, 35(12) Scand. J. Gastroenterol., 1266-1271 (Dec. 2000).
G. Önning et al., *Influence of a drink containing different antioxidants and* Lactobacillus plantarum *299v on plasma total antioxidant capacity, selenium status and faecal microbial foral*, 54(4) Int. J. Food Sci. Nutr. 281-289 (Jul. 2003).
Japanese Office Action mailed on Oct. 25, 2011, in Japanese Patent Application Serial No. 2008-519228.
*Iron absorption from capsules containing freeze dried lactobacilli Lp299v and iron*, AIKN Apr. 4, 2014 ("Report 1") (2014).
*Iron absorption from capsules containing freeze dried lactobacilli Lp299v and iron*, AIKN Jul. 1, 2014 ("Report 2") (2014).
Clinical trials testing *L. plantarum* in human subjects, as described in *Iron absoprtion from capsules containing freeze dried* Lactobacillus plantarum *DSM 9843 (LP299V®)and iron*("Poster") (2014).
A comparative in vitro test report on calcium uptake and transport, as described in *Calcium uptake and transport in Caco-2 cells in the presence of L* plantarum, Apr. 6, 2009 ("Report 3") (2009).
Adlerberth et al. (1996). A mannose-specific adherence mechanism in Lactobacillus plantarum conferring binding to the human colonic cell line HT-29. Appl Environ Microbiol. Jul. 1996;62(7):2244-51.
Ahrné et al. (1998). The normal Lactobacillus flora of healthy human rectal and oral mucosa. J Appl Microbiol. 1998 Jul;85(1):88-94.
Antonsson el al. (2001). A comparison between the microflora of Herrgård cheese from three different dairies. International Dairy Journal 11:285-291.
Bengmark et al. (1996). Nutritional support to prevent and treat multiple organ failure. World J Surg. May 1996;20(4):474-481.
Berggren et al. (2011). Randomised, double-blind and placebo-controlled study using new probiotic lactobacilli for strengthening the body immune defence against viral infections. Eur J Nutr. Apr. 2011;50(3):203-210. doi: 10.1007/s00394-010-0127-6. Epub Aug. 28, 2010.
Bering et al. (2006). A lactic acid-fermented oat gruel increases non-haem iron absorption from a phytate-rich meal in healthy women of childbearing age. Br J Nutr. Jul. 2006;96(1):80-85.
Bering et al. (2007). Viable, lyophilized lactobacilli do not increase iron absorption from a lactic acid-fermented meal in healthy young women, and no. iron absorption occurs in the distal intestine. Br J Nutr. Nov. 2007;98(5):991-997. Epub Sep. 3, 2007.
Busch et al. (2013). Randomized, Double Blind and Placebo Controlled Study Using a Combination of Two Probiotic Lactobacilli to Alleviate Symptoms and Frequency of Common Cold. Food Nutr Sci. Nov. 2013;4(11A):13-20. doi: 10.4236/fns.2013.411A003.
Cunningham-Rundles et al. (2002). Development of immunocompetence: role of micronutrients and microorganisms. Nutr Rev. May 2002;60(5 Pt 2):S68-72.
Ducrotté et al. (2012). Clinical trial: *Lactobacillus plantarum* 299v (Dsm 9843) improves symptoms of irritable bowel syndrome. World J Gastroenterol. Aug. 2012;18(30):4012-4018. doi: 10.3748/wjg.v18.i30.4012.
Eccles (2005). Understanding the symptoms of the common cold and influenza. Lancet Infect Dis. Nov. 2005;5(11):718-725.
Fendrick et al. (2003). The economic burden of non-influenza-related viral respiratory tract infection in the United States. Arch Intern Med. Feb. 24, 2003;163(4):487-494.
Gastrointestinal disorders. 2015.
Hoppe et al. (2015). Probiotic strain *Lactobacillus plantarum* 299v increases iron absorption from an iron-supplemented fruit drink: a double-isotope cross-over single-blind study in women of reproductive age. Br J Nutr. Oct. 28, 2015;114(8):1195-1202. doi: 10.1017/S000711451500241X.
Immune system. 2015.
Increased iron absorption. Nov. 2015.
Johansson et al. (1993). Administration of different Lactobacillus strains in fermented oatmeal soup: in vivo colonization of human intestinal mucosa and effect on the indigenous flora. Appl Environ Microbiol. Jan. 1993;59(1):15-20.
Johansson et al. (1998). Survival of Lactobacillus plantarum DSM 9843 (299v), and effect on the shortchain fatty acid content of faeces after ingestion of a rose-hip drink with fermented oats. Int J Food Microbiol. Jun. 30, 1998;42(1-2):29-38.
Karlsson et al. (2010). Probiotic therapy to men with incipient arteriosclerosis initiates increased bacterial diversity in colon: a randomized controlled trial. Atherosclerosis. Jan. 2010;208(1):228-233. doi: 10.1016/j.atherosclerosis.2009.06.019. Epub Jun. 18, 2009.
King et al. (2014). Effectiveness of probiotics on the duration of illness in healthy children and adults who develop common acute respiratory infectious conditions: a systematic review and meta-analysis. Br J Nutr. Jul. 14, 2014;112(1):41-54. doi: 10.1017/S0007114514000075. Epub Apr. 29, 2014.
Kirkpatrick (1996). The common cold. Prim Care. Dec. 1996;23(4):657-675.
Klarin et al. (2008). *Lactobacillus plantarum* 299v reduces colonisation of *Clostridium difficile* in critically ill patients treated with antibiotics. Acta Anaesthesiol Scand. Sep. 2008;52(8):1096-1102. doi: 10.1111/j.1399-6576.2008.01748.x.
Krag et al. (2012). Safety and efficacy of Profermin® to induce remission in ulcerative colitis. World J Gastroenterol. Apr. 21, 2012;18(15):1773-1780. doi: 10.3748/wjg.v18.i15.1773.
Krag et al. (2013). Profermin is efficacious in patients with active ulcerative colitis—a randomized controlled trial. Inflamm Bowel Dis. Nov. 2013;19(12):2584-2592. doi: 10.1097/01.MIB.0000437046.26036.db.
Lavasani et al. (2010). A novel probiotic mixture exerts a therapeutic effect on experimental autoimmune encephalomyelitis mediated by IL-10 producing regulatory T cells. PLoS One. Feb. 2, 2010;5(2):e9009. doi: 10.1371/journal.pone.0009009.
Lenoir-Wijnkoop et al. (2015). Public health and budget impact of probiotics on common respiratory tract infections: a modelling study. PLoS One. Apr. 10, 2015;10(4):e0122765. doi: 10.1371/journal.pone.0122765. eCollection 2015.
Lomax et al. (2009). Probiotics, immune function, infection and inflammation: a review of the evidence from studies conducted in humans. Curr Pharm Des. 2009;15(13):1428-1518.
Lönnermark et al. (2010). Intake of *Lactobacillus plantarum* reduces certain gastrointestinal symptoms during treatment with antibiotics. J Clin Gastroenterol. Feb. 2010;44(2):106-112. doi: 10.1097/MCG.0b013e3181 b2683f.
Mack et al. (1999). Probiotics inhibit enteropathogenic *E. coli* adherence in vitro by inducing intestinal mucin gene expression. Am J Physiol. Apr. 1999;276(4 Pt 1):G941-950.
Mack et al. (2003). Extracellular MUC3 mucin secretion follows adherence of Lactobacillus strains to intestinal epithelial cells in vitro. Gut. Jun. 2003;52(6):827-833.
Mao, D. (Mar. 15, 2005). The effect of iron fortified fermented milk on iron absorption and anaemia prevention. Chinese Advanced Masters Thesis Database, Medical Science and Technology Series, Issue No. 1, pp. 12-22, 31, 33.
Mao, D. (Mar. 15, 2005). The effect of iron fortified fermented milk on iron absorption and anaemia prevention. Chinese Advanced Masters Thesis Database, Medical Science and Technology Series, Issue No. 1, pp. 12-22, 31, 33; Partial English Translation.
McCracken et al. (2002). TNF-alpha sensitizes HT-29 colonic epithelial cells to intestinal lactobacilli. Exp Biol Med (Maywood). Sep. 2002;227(8):665-670.
McnNaught et al. (2005). A prospective randomised trial of probiotics in critically ill patients. Clin Nutr. Apr. 2005;24(2):211-219.
Metabolic syndrome. 2015.
Molin (2015) *Lactobacillus plantarum* HEAL19. Oct. 29, 2015.
Molin (2015) *Lactobacillus plantarum* HEAL9. Oct. 29, 2015.
Molin (2015) *Lactobacillus rhamnosus* 271. Nov. 4, 2015.
Molin (2015) *Lactobacillus plantarum* 299. Jun. 10, 2015.
Molin (2015) *Lactobacillus plantarum* 299v. Oct. 29, 2015.
Molin (2015) *Lactobacillus paracasei* 8700:2. Oct. 29, 2015.

(56) References Cited

OTHER PUBLICATIONS

Niedzielin et al. (2001). A controlled, double-blind, randomized study on the efficacy of *Lactobacillus plantarum* 299V in patients with irritable bowel syndrome. Eur J Gastroenterol Hepatol. Oct. 2001;13(10):1143-1147.

Nobaek et al. (2000). Alteration of intestinal microflora is associated with reduction in abdominal bloating and pain in patients with irritable bowel syndrome. Am J Gastroenterol. May, 2000;95(5):1231-1238.

Osteoporosis. Nov. 2015.

Rask et al. (2013). Differential effect on cell-mediated immunity in human volunteers after intake of different lactobacilli. Clin Exp Immunol. May 2013;I 72(2):32I -332. doi: 10.1111/cei.12055.

Stress and recovery. Nov. 2015.

Vasquez et al. (2005). Oral administration of *Lactobacillus* and *Bifidobacterium* strains of intestinal and vaginal origin to healthy human females: Re-isolation from faeces and vagina. Microb Ecol Health D 2005;17(1):15-20.

Wurzelmann, J.I., et al. (1996). Iron intake and the risk of colorectal cancer. Cancer Epidemiol Biomarkers Pre; 5(7):503-507.

\* cited by examiner

METHODS OF TREATING ANEMIA AND INCREASING THE ABSORPTION OF NON-HEME IRON BY ADMINISTRATION OF *LACTOBACILLUS PLANTARUM*

TECHNICAL FIELD OF THE INVENTION

The present invention relates to the use of at least one specified strain of *Lactobacillus plantarum* for increasing the absorption of metals/metal ions in a mammal. The invention further relates to the use of at least one specified strain of *Lactobacillus plantarum* for the preparation of a pharmaceutical composition and to compositions comprising at least one specified strain of *Lactobacillus plantarum*.

BACKGROUND ART

Iron deficiency and low iron stores are prevalent in infants, adolescents, and women of childbearing age in both Western and developing countries. One cause of iron deficiency is the low iron bioavailability from foods, which is partly due to inhibiting factors in the diet, such as phytic acid and phenolic compounds. Other factors enhance iron absorption. These include muscle tissue, ascorbic acid and certain other organic acids.

Phytic acid is found mainly in the fibre fraction of cereals, vegetables and fruit. The inhibiting effect of phytic acid is due to the formation of insoluble complexes with iron at intestinal pH. A reduction in the content of phytic acid in those foods or a way to inhibit complex binding with iron would eliminate the problem with low iron absorption from foods that are rich in iron and which otherwise are regarded as healthy and nutritious. Phytic acid is hydrolyzed by phytases found in certain plants, microorganisms, and animal tissues. Most cereal phytases have a pH optimum in the range 5.0-5.6. By lowering the pH of foods the endogenous phytases in cereals and vegetables may be activated and thereby reduce the content of phytic acid, as in e.g. sourdough fermentation.

EP 1 003 532 describes the use of lactobacilli in the preparation of non-fermented enteral compositions for facilitating or increasing the absorption of minerals from the diet. The only experiments performed therein in supporting said claimed absorption is an in vitro model of calcium responses or transportation of calcium using Caco-2 intestinal lines (a carcinogenic cell line).

In accordance with the present invention metal/metal ion absorption has been performed in an in vivo study in humans. It has surprisingly been found that not all lactobacilli have the desired absorption as claimed in EP 1 003 532. It has further been found that certain specific strains of *Lactobacillus plantarum* achieve a surprisingly good absorption of said metals/metal ions in the body.

SUMMARY OF THE INVENTION

The present invention relates in one aspect to the use of at least one strain of *Lactobacillus plantarum* chosen from the group comprising *Lactobacillus plantarum* 299, DSM 6595, *Lactobacillus plantarum* 299v, DSM 9843, *Lactobacillus plantarum* HEAL 9, DSM 15312, *Lactobacillus plantarum* HEAL 19, DSM 15313, *Lactobacillus plantarum* HEAL 99, DSM 15316, and a part thereof, for the preparation of a composition for increasing the absorption of at least one kind of metal/metal ion in a mammal, preferably a human.

By providing the use of above mentioned compositions the general health of mammals, preferably humans and especially women and children, may be significantly enhanced by the increased absorption of said metals/metal ions in the body. Thus, the human body can make use of a larger portion of the metals/metal ions in the food consumed, leading to a better general health condition and the individuals will feel better. A further advantage of the invention is that the individuals need not increase the consumption of the respective metals/metal ions, such as Fe, in order to achieve the desired absorption. It will take place without addition of supplementary amounts of the respective metals/metal ions. Thus, negative effects that may arise from an increased consumption of for instance Fe, which before has been the manner to increase the uptake of a certain metal, can be avoided. Examples of such negative effects which can be avoided with the present invention are colon cancer, i.e. it has been seen that a too high consumption of Fe may lead to colon cancer, see for instance "Iron intake and the risk of colorectal cancer", Wurzelmann J I et al, in Cancer Epidemiol Biomarkers Prev. 1996 July; 5(7):503-7.

The invention in another aspect relates to a method for increasing the absorption of at least one kind of metal/metal ion in a mammal, preferably human, by administering a composition comprising at least one strain of *Lactobacillus plantarum* chosen from the group comprising *Lactobacillus plantarum* 299, DSM 6595, *Lactobacillus plantarum* 299v, DSM 9843, *Lactobacillus plantarum* HEAL 9, DSM 15312, *Lactobacillus plantarum* HEAL 19, DSM 15313, and *Lactobacillus plantarum* HEAL 99, DSM 15316 and a part thereof.

The invention in a further aspect relates to the use of at least one strain of *Lactobacillus plantarum* chosen from the group comprising *Lactobacillus plantarum* 299, DSM 6595, *Lactobacillus plantarum* 299v, DSM 9843, *Lactobacillus plantarum* HEAL 9, DSM 15312, *Lactobacillus plantarum* HEAL 19, DSM 15313, and *Lactobacillus plantarum* HEAL 99, DSM 15316, and a part thereof, for the preparation of a pharmaceutical composition for treatment of anemia, osteoporosis or any other disorder where a deficiency of at least one of the metals/metal ions chosen from the group comprising Fe, Zn, Ca and Mg and ions thereof is a problem.

Any disorder or disease in which there is a deficiency in one of the metals/metal ions mentioned above may be treated or prevented with the use of a pharmaceutical composition according to the invention.

The invention in yet another aspect relates to a composition comprising at least one strain of *Lactobacillus plantarum* chosen from the group comprising *Lactobacillus plantarum* 299, DSM 6595, Lactobacillus plantarum 299v, DSM 9843, *Lactobacillus plantarum* HEAL 9, DSM 15312, *Lactobacillus plantarum* HEAL 19, DSM 15313, *Lactobacillus plantarum* HEAL 99, DSM 15316, and a part thereof, in combination with at least one metal/metal ion chosen from the group comprising Fe, Zn, Ca, Mg and ions thereof.

DESCRIPTION OF THE INVENTION

In one embodiment of the invention said at least one metal/metal ion is chosen from the group comprising Fe, Zn, Ca and Mg and ions thereof. It is further possible that said at least one metal/metal ion is associated with another element or complex bound with another element. Thus, the increased absorption may take place with any of the mentioned metals/metal ions, even though the metals/metal ions exist in another form.

In another embodiment of the invention said at least one strain may be viable, inactivated or suppressed, or dead, as long as the desired increased absorption of the metals/metal ions is obtained. Further, said at least one strain may be genetically modified.

In another embodiment of the invention said composition comprises a carrier material. Said carrier material may be chosen from the group comprising oat meal gruel, lactic acid fermented foods, resistant starch, inulins, fructans, and sugar alcohols, dietary fibres, carbohydrates, proteins, glycosylated proteins, and lipids. The carrier may further be a combination of above mentioned carriers, providing a mixture of for instance a lipid, a carbohydrate and a protein. Said carrier material may be fermented with one or more of the strains chosen from the group comprising *Lactobacillus plantarum* 299, DSM 6595, *Lactobacillus plantarum* 299v, DSM 9843, *Lactobacillus plantarum* HEAL 9, DSM 15312, *Lactobacillus plantarum* HEAL 19, DSM 15313, and *Lactobacillus plantarum* HEAL 99, DSM 15316.

In a further embodiment of the invention said composition is chosen from the group comprising a food product, a dietary supplement, a nutritional product, a functional food, and a medical food. Said food product may be chosen from the group comprising beverages, yoghurts, juices, ice creams, breads, biscuits, cereals, health bars, and spreads. The mentioned compositions may be fermented or non-fermented, the fermented compositions being preferred.

In yet another embodiment said composition comprises at least one of the metals/metal ions chosen from the group comprising Fe, Zn, Ca and Mg and ions thereof. By including the metals/metal ions in the composition to be taken an even higher absorption may be observed in view of the increased concentration.

In another embodiment said at least one strain in the composition is present in an amount from about $1\times10^6$ to about $1\times10^{14}$ CFU, preferably $1\times10^8$ to $1\times10^{12}$, and more preferably $1\times10^9$ to $1\times10^{11}$.

In a further embodiment of the invention said pharmaceutical composition is a liquid formulation or a solid formulation. The solid formulation may be chosen from the group comprising tablets, sucking tablets, sweets, chewing tablets, chewing gums, capsules, sachets, powders, granules, coated particles and coated tablets, enterocoated tablets and capsules, and melting strips and films. Said liquid formulation may be chosen from the group comprising oral solutions, suspensions, emulsions and syrups.

In another embodiment said pharmaceutical composition comprises at least one kind of the metals/metal ions chosen from the group comprising Fe, Zn, Ca and Mg and ions thereof. Said at least one metal/metal ion may further be associated with another element or complex bound with another element as long as desired absorption is obtained.

Said at least one strain in the pharmaceutical composition may be viable, inactivated or suppressed, or dead. Said at least one strain may also be genetically modified. It is further possible that the strains used are a combination of the above, i.e. one strain is viable and another is inactivated for instance.

In another embodiment said at least one strain in the pharmaceutical composition is present in an amount from about $1\times10^6$ to about $1\times10^{14}$ CFU, preferably $1\times10^8$ to $1\times10^{12}$, and more preferably $1\times10^9$ to $1\times10^{11}$.

In yet another embodiment there is provided a composition comprising at least one strain of Lactobacillus plantarum chosen from the group comprising *Lactobacillus plantarum* 299, DSM 6595, *Lactobacillus plantarum* 299v, DSM 9843, *Lactobacillus plantarum* HEAL 9, DSM 15312, *Lactobacillus plantarum* HEAL 19, DSM 15313, *Lactobacillus plantarum* HEAL 99, DSM 15316, and a part thereof, in combination with at least one metal/metal ion chosen from the group comprising Fe, Zn, Ca, Mg and ions thereof, wherein said at least one metal/metal ion is associated with another element or complex bound with another element. Said at least one strain may be viable, inactivated or suppressed, or dead. Said at least one strain may also be genetically modified. By administering a composition of the invention the general health of humans may be promoted. Especially the health of menstruating women or other persons with low iron store may be promoted by the use of the compositions of the invention. Said humans need not be anaemic, but the general health would be enhanced.

In a further embodiment said composition comprises a carrier material, wherein said carrier material is chosen from the group comprising oat meal gruel, lactic acid fermented foods, resistant starch, dietary fibres, inulins, fructans, and sugar alcohols, carbohydrates, proteins, glycosylated proteins, and lipids. Said carrier material may further be fermented with one or more of the strains chosen from the group comprising *Lactobacillus plantarum* 299, DSM 6595, *Lactobacillus plantarum* 299v, DSM 9843, *Lactobacillus plantarum* HEAL 9, DSM 15312, *Lactobacillus plantarum* HEAL 19, DSM 15313, and *Lactobacillus plantarum* HEAL 99, DSM 15316.

In one embodiment of the invention said composition is chosen from the group comprising a food product, a dietary supplement, a nutritional product, a functional food, and a medical food. Said food product may be chosen from the group comprising beverages, yoghurts, juices, ice creams, breads, biscuits, cereals, health bars, and spreads. Said at least one strain in the composition may be present in an amount from about $1\times10^6$ to about $1\times10^{14}$ CFU, preferably $1\times10^8$ to $1\times10^{12}$, and more preferably $1\times10^9$ to $1\times10^{11}$.

A "part" of a strain in the present specification is meant to be a part of a bacterial cell such as a part of DNA, cell wall, cell membrane, or any other part of the bacterial cell having the activity required to increase absorption of metal/metal ions as described herein. A part of a strain in the present context could also be a total or partial homogenate.

A "metal/metal ion" as used herein is meant a pure metal and metal ion, respectively, such as Fe, Zn, Ca and Mg and $Fe^{2+}$, $Fe^{3+}$ $Zn^{2+}$, $Ca^{2+}$ and $Mg^{2+}$. The absorption disclosed herein may naturally take place even if said metals/metal ions are in another form such as complex bound or associated with other element.

"Complex bound with an element" or "associated with an element" is meant herein as any form the metals/metal ions may exist and the desired absorption does still take place.

DETAILED DESCRIPTION OF EMBODIMENTS
OF THE INVENTION

EXPERIMENTAL

Experiment 1

In the present study, the effect of *L. plantarum* 299v and its fermentation products, lactic acid and acetic acid, on nonheme iron absorption from a low iron bioavailability meal using a crossover design have been studied. Four different oat gruels were included to test the specific effect of *L. plantarum* 299v and the organic acids: A fermented oat gruel with active *L. plantarum* 299v, a pasteurized fermented oat gruel with the fermentation products but inactivated bacteria, a pH-adjusted non-fermented oat gruel, and a non-fermented oat gruel with added organic acids.

Subjects and Methods

Subjects

Seventy women volunteered and were screened 2-4 wk before the study, and 24 women were selected for the study on the basis of relatively low iron stores but non-anaemic, i.e. a serum ferritin concentration ≤40 µg/L and a hemoglobin concentration ≥110 g/L. The 24 volunteers were healthy young women with a mean age (±SD) of 25±4 y, mean weight of 62±7 kg, and a mean body mass index of 21.3±1.9 kg/m². All subjects were non-smokers and none of them were pregnant or lactating or took any vitamin or mineral supplements for ≥2 mo before or during the study. Eighteen subjects used oral contraceptives, but none of the subjects were routinely taking any other medication. Blood donation was not allowed for ≥2 mo before or during the study. Each participant received oral and written information about the study before written consent was obtained. The study was approved by the Municipal Ethical Committee of Copenhagen and Frederiksberg, Denmark (file no. KF 01-219/03) and the National Institute of Radiation Hygiene, Denmark.

Experimental Design

The study was a completely randomized, double-blinded cross-over trial, in which each subject was served 4 test meals: (A) a fermented oat gruel, (B) a pasteurized fermented oat gruel, (C) a non-fermented oat gruel (pH adjusted with lactic acid), and (D) a non-fermented oat gruel with added organic acids (lactic acid and acetic acid).

Iron absorption from the 4 test meals was determined with the dual label extrinsic tag method. Using this method iron absorption from the 4 test meals was measured by measuring iron absorption from 2 test meals simultaneously in each of 2 periods. The two different test meals in each period were extrinsically labelled with $^{55}$Fe and $^{59}$Fe, respectively, and served twice on 4 consecutive mornings to minimize potential effects of day-to-day variation, e.g. in the order ABBA. All 12 serving orders were used and assigned randomly to subjects, so that all test meals occurred equal times as first meal served in a period. This was important to be able to validate the possible carry-over effect of the fermented oat gruel with the live colonizing bacteria within a period.

The activities of both isotopes were measured in a blood sample 18 days after ingestion, hereafter the second period was carried out with the remaining test meals. Residual isotope activity from the first period was subtracted from the isotope activity levels in the blood sample from the second period.

Composition of Test Meals and Serving Procedure

The oat gruels were made of oatmeal mixed with water, then treated with enzymes and pasteurized (obtained by Probi AB). Oat gruel A was then fermented with L. plantarum 299v (DSM 9843, viable count $1.1\times10^9$ cfu/g) [20]. Oat gruel B was a pasteurized oat gruel A (viable count <10 cfu/g), oat gruel C was the non-fermented basic oat gruel acidified with L-lactic acid to an equivalent pH as oat gruel A, B, and D, and oat gruel D was the non-fermented basic oat gruel added the organic acids DL-lactic acid and acetic acid to an equivalent of what was expected to be produced in oat gruel A during the fermentation. For each test meal 100 g oat gruel (A, B, C, or D) was served with a 140 g whole-wheat roll (60.0 g wheat flour, 20.0 g whole-wheat flour, 2.0 g salt, 2.0 g yeast, 16.0 g rapeseed oil, 40.0 g ultra pure water) with 10 g butter and a glass of ultra pure water (200 mL). The oat gruels were prepared from one batch and stored cold (4° C.) until serving. The whole-wheat rolls were prepared in one batch, stored frozen and reheated in an oven at 200° C. for 10 min before serving.

The test meals were served in the morning after 12 h of fasting. Intake of a maximum of 0.5 L water was allowed overnight. Moderate or hard physical activity or the intake of any alcohol or medication was not allowed during the 12 h before intake of the test meals. After consuming the test meals, the subjects were not allowed to eat or drink for 2 h and intake of alcohol was prohibited for 24 h. The subjects filled in a questionnaire in connection with each test meal to ensure that they adhered to all procedures, and they were instructed to eat and drink alternately and to rinse the glass containing the oat gruel thoroughly with the water to ensure complete intake of the isotope dose. A staff member ensured that everything was eaten.

During the experimental period the subjects filled out a detailed questionnaire on their daily eating habits.

Isotopes and Labelling Procedure

All meals were extrinsically labelled by adding 1 mL isotope solution [$^{55}$FeCl$_3$ (NEN Life Science Products, Inc., Boston, Mass.) or $^{59}$FeCl$_3$ (Amersham Biosciences Corp., Piscataway, N.J.) in 0.1 mol/L HCl] directly to the oat gruels 18 h before serving for isotope exchange. In the first period each dose contained 37 kBq $^{55}$FeCl$_3$ or $^{59}$FeCl$_3$ and in the second period 74 kBq $^{55}$FeCl$_3$ or $^{59}$FeCl$_3$.

Dietary Analyses

The 4 oat gruels and the bread were freeze-dried, homogenized, and analyzed in duplicates for total iron, calcium, zinc and phytic acid. The energy content was calculated with the use of a national food-composition database (Danish Tables of Food Composition, DANKOST 2000, version 1.20, Herlev, Denmark). Total iron, calcium, and zinc were determined by atomic absorption spectrophotometry (Spectra-AA 200, Varian, Mulgrave, Australia) after wet-ashing in a MES 1000 Solvent Extraction System (CEM Corp., Matthews, N.C.) with 65% (w/v) suprapure nitric acid (Merck KGaA, Darmstadt, Germany). A typical diet Standard Reference Material 1548a (National Institute of Standards and Technology, Gaithersburg, Md.) was used as the reference for iron (mean±SD: 35.3±3.77 µg/g), calcium (1.96±0.11 mg/g), and zinc (24.6±1.79 µg/g), and the analyzed values were 33.38 µg/g, 2.00 mg/g, and 23.25 µg/g, respectively. Phytic acid was analyzed as individual inositol tri- to hexaphosphates (IP$_{3-6}$)[1] by high-performance ion chromatography. The concentration of organic acids in the oat gruels was determined by capillary gas chromatography.

Determination of Iron Status

Restrictions on intake and exercise before the blood samples were as described for the test meals. Blood samples were drawn from the cubital vein after the subjects had rested for 10 min in a supine position. Hemoglobin analysis was carried out on venous blood (3.5 mL) collected in tubes containing dissolved EDTA (Vacutainer system, Becton Dickinson, Franklin Lakes, N.J.) by using a Sysmex KX-21 automated hematology analyzer (Sysmex America Inc., Mundelein, Ill.) and appropriate controls (Eight check-3WP, 22490822, Sysmex America Inc.). Intraassay and interassay variations were 0.5% (n=12) and 0.6% (n=27), respectively. Serum ferritin and $\alpha_1$-antichymotrypsin (ACT) analyses were carried out on venous blood (5.0 mL) collected in plain tubes (Vacutainer system, Becton Dickinson). Serum ferritin was determined on an Immulite 1000 analyzer (Diagnostic Products Corporation, Los Angeles, Calif.) by a chemiluminescent immunometric assay, and appropriate reference sera were also analyzed (3$^{rd}$ International standard for ferritin (80/578), WHO, NIBSC, South Mimms, United Kingdom).

Intraassay and interassay variations were 2.7% (n=15) and 5.0% (n=15), respectively. ACT was determined on a Cobas Mira analyzer (Roche Diagnostic Systems, F. Hoffman-La Roche Ltd., Basel, Switzerland) with use of an immunoturbidimetric technique and appropriate reference sera were also analyzed (European Commission certified reference material 470, no. 11924, IRMM, Geel, Belgium). Intraassay and interassay variations were 1.4% (n=12) and 3.2% (n=14), respectively.

Determination of Nonheme Iron Absorption

Activity of $^{55}$Fe and $^{59}$Fe was determined from blood samples (60 mL) collected in tubes containing heparin as anticoagulant (Vacutainer system, Becton Dickinson). Simultaneous determination of $^{55}$Fe and $^{59}$Fe was performed by dry-ashing followed by recrystallization and solubilization before counting in a Tricarb 2100TR Liquid Scintillation Analyzer (Packard Instruments, Meriden, Conn.) with automatic quench correction by the method described previously.

Statistical Analysis

Nonheme iron absorption data were converted to logarithms before statistical analysis, and the results were reconverted to antilogarithms. All data used for statistical analyses were normally distributed, with variance homogeneity tested by plots of residuals. The nonheme iron absorption from the different meals was compared using a linear mixed model with log (nonheme iron absorption) as the dependent variable, meal, alternate meal, and ferritin as independent fixed variables and subject and subject×period interaction as random effects:

$$\text{Log (nonheme iron absorption)} = \mu(\text{meal}_i) + \alpha(\text{alternate meal}_i) + b \times \text{ferritin}_i + A(\text{subject}_i) + B(\text{subject}_i \times \text{period}_i) + \epsilon_i$$

Data are presented as estimates of least-squares means and differences betweens estimates of means with 95% CIs. The statistical analysis was performed with the SAS statistical software package, version 8.2 (SAS Institute Inc., Cary, N.C.), and values were considered significantly different for P<0.05.

Results

Composition of the Test Meals

The composition of the test meals and the contents of organic acids in the oat gruels are given in Table 1 below.

TABLE 1

Composition of the test meals, including a whole-wheat roll with butter, and pH and concentrations of organic acids in the oat gruels

|  | Fermented oat gruel A | Pasteurized fermented oat gruel B | Basic oat gruel (pH adjusted) C | Oat gruel with organic acids D |
|---|---|---|---|---|
| Energy (MJ) | 2.5 | 2.5 | 2.5 | 2.5 |
| Nonheme iron (mg) | 2.8 | 2.8 | 2.5 | 2.8 |
| Phytate[1] (mg) | 403 | 393 | 388 | 344 |
| (µmol) | 645 | 635 | 621 | 551 |
| Calcium (mg) | 39.6 | 42.2 | 39.5 | 41.1 |
| Zinc (mg) | 2.2 | 2.2 | 2.1 | 2.2 |
| Lactic acid (µmol/g) | 110 | 89 | 61 | 43 |
| Acetic acid (µmol/g) | 4.0 | 3.7 | 1.1 | 3.7 |

TABLE 1-continued

Composition of the test meals, including a whole-wheat roll with butter, and pH and concentrations of organic acids in the oat gruels

|  | Fermented oat gruel A | Pasteurized fermented oat gruel B | Basic oat gruel (pH adjusted) C | Oat gruel with organic acids D |
|---|---|---|---|---|
| Succinic acid (µmol/g) | 0.3 | 0.3 | 0 | 0 |
| pH | 3.9 | 4.1 | 4.2 | 4.0 |

[1]Represents individual inositol tetra- to hexaphosphates

Iron Status and Nonheme Iron Absorption

The subjects' hemoglobin concentrations were in the range 111-137 g/L and serum ferritin concentrations in the range 12-40 µg/L. As the serum ferritin concentration is sensitive to inflammation, the acute phase protein ACT was determined in serum as a marker of an acute phase response. The concentrations were in the region 0.20-0.37 g/L, indicating no acute phase response (ACT<0.6 g/L) and therefore valid measurement of the subjects iron status.

The nonheme iron absorption from the 4 test meals calculated from the mixed linear model analysis is given in Table 2, see below.

TABLE 2

Nonheme iron absorption from the meals containing the 4 different oat gruels

|  | Fermented oat gruel | Pasteurized fermented oat gruel | Oat gruel with organic acids | Basic oat gruel |
|---|---|---|---|---|
| Nonheme iron absorbed in blood (%)[1] | 1.1 (0.8, 1.5)* | 0.6 (0.4, 0.7) | 0.5 (0.4, 0.7) | 0.5 (0.4, 0.7) |
| Test meal: control meal[2] | 2.2 (1.7, 2.9)* | 1.1 (0.8, 1.4) | 1.0 (0.8, 1.3) | — |

[1]Geometric means of least squares estimates from the mixed linear model analysis with 95% CI in parentheses, n = 24
[2]Geometric means of estimates of differences from the mixed linear model analysis with 95% CI in parentheses, n = 24
*Values are significantly different from all the other values in each row (P < 0.0001)

The results show a highly significant effect of the test meal with the fermented oat gruel when comparing both absolute nonheme iron absorption values and the ratios relative to the pH-adjusted non-fermented oat gruel meal (P<0.0001), in which the inter-individual variations are taken into account.

As *L. plantarum* 299v can colonize the human intestinal mucosa for about 2 weeks and as the test meal with the fermented oat gruel increased nonheme iron absorption the specific carry-over effect of this test meal on the following ingested test meal within a period was evaluated. No general carry-over effect of test meals was seen, but looking at the specific effect of the meal with the fermented oat gruel the carry-over effect was close to reach statistical significance (P=0.06).

The absorption ratios from the different test meals showed a highly significant increase in nonheme iron absorption from the test meal with the lactic acid fermented oat gruel, whereas there was no effect of the pasteurized fermented oat gruel meal and the non-fermented oat gruel meals, serving as different controls. As the content of iron and phytate in the 4 test meals was constant, this significant effect can be directed to an effect of the fermentation of *L. plantarum*

299v. Whether it is an effect of the active *L. plantarum* 299v or an effect of the organic acids produced during the fermentation should be determined from comparisons of the absorption ratio for the meal with the fermented oat gruel with the absorption ratios for the meals with the inactivated *L. plantarum* 299v (pasteurized fermented oat gruel) and the non-fermented oat gruel with added organic acids, as lactic acid and acetic acid was added to the latter in concentrations that are normally produced during the fermentation process. The results from the analysis of organic acids show that it wasn't possible to reach similar levels of organic acids in the 3 oat gruels at the time of ingestion (table 2). The meal with the smallest difference in concentrations of organic acids compared to the fermented oat gruel was the pasteurized fermented oat gruel, in which the concentrations of lactic acid and acetic acid was 19% and 8% lower, respectively. When comparing the iron absorption ratios for these 2 meals the ratio was reduced to 50% for the pasteurized fermented oat gruel. As the level of lactic acid in the oat gruel with added organic acids was 52% lower than in the pasteurized fermented oat gruel and the absorption ratio was reduced with only 9%, it is unlikely that the increase in iron absorption in the fermented oat gruel was due mainly to an effect of the organic acids. The results of the present study therefore indicate that the active lactic acid bacterium, *L. plantarum* 299v ($1.1 \times 10^{11}$ cfu), was able to increase nonheme iron absorption from a low iron bioavailability meal in young women.

Iron absorption is normally described to occur in the duodenum and proximal small intestine. Small organic acids from the food, such as lactic acid and acetic acid from the pasteurized fermented oat gruel and the oat gruel with added organic acids, is very quickly absorbed in the gastrointestinal tract. A possible explanation of the enhanced nonheme iron absorption from the fermented oat gruel could be the colonization of *L. plantarum* 299v in the mucosa of the most proximal small intestine or possibly colon, where local production of the organic acids by the active bacterium may both decrease the local pH and the lactic acid may form soluble complexes with iron as has been described by Derman et al. This hypothesis may be strengthened by the fact that the carry-over effect of the meal with the fermented oat gruel was close to reach significance (P=0.06), indicating an effect of *L. plantarum* 299v on nonheme iron absorption from the meals ingested the following days where the bacterium still colonized the intestine.

When comparing the absorption ratios for the test meals with fermented oat gruel, the pasteurized fermented oat gruel, and the oat gruel with added organic acids (as described above) it seems clear that the increase in absorption from the test meal with the fermented oat gruel can not be assigned to an effect of the organic acids alone, as has been hypothesised before, but that there is a specific effect of the active *L. plantarum* 299v.

Experiment 2

Reagents. All reagents were from GTF (Göteborg, Sweden) unless otherwise indicated.

Caco-2 Cell Culture. Caco-2 cells were obtained from the American Type Culture Collection (Rockville, Md.) at passage 17 and used for experiments at passages 20-35. Stock cultures were maintained in Dulbecco's modified α essential medium (DMEM) supplemented with 20% (v/v) fetal calf serum (FSC), 100 units/L penicillin G, and 100 mg/L streptomycin at 37° C. in a huminified atmosphere of 95% air-5% CO2. The growth medium was changed every second to third day. Cells were split at ~80% confluence using 0.5 g/L trypsin with 0.5 mmol/L EDTA in Dulbecco's phosphate buffered saline (PBS). Prior to the experiments, 100000 cells in 0.5 mL of supplemented DMEM were seeded on 0.4 µm microporous polycarbonate membrane inserts (1 cm2 Tranwell inserts; Corning, Acton, Mass.). The basolateral chamber contained 1.5 mL of supplemented DMEM. The medium on both sides of the filter insert was changed every 2-3 days. All iron uptake and transfer experiments were performed 14-17 days postseeding.

Bacterial cultures. *Lactobacillus plantarum* 299v (DSM9843), (5), *Lactobacillus plantarum* 299, (1), *Lactobacillus plantarum* Heal 9 (DSM 15312), (2), Lactobacillus plantarum Heal 19 (DSM15313), (4), *Lactobacillus plantarum* 299v mutant (AMJ1277), (3) and *Lactobacillus reuteri*, (6) were cultured in MRS broth at a rotary shaker (37° C., 200 rpm). The bacteria were harvested in the exponential phase ($OD_{600, max}$=1.3). The volume of cell culture corresponding to a certain cell-number was calculated from a predetermined standard curve. The cells were spinned down at 5000 rpm (Sorvall heraeus, multifuge) for 2 minutes and later resuspended in a transport solution of HBSS (PAA), HEPES 2.5% (1 M, PAA) and $FeCl_3$ 10 µM. The trial was performed with a cell concentration of $6.7 \times 10^7$ cells/ml for all species but *Lactobacillus reuteri* which was added in a concentration of $3.35 \times 10^7$ cells/ml. The trial was repeated twice.

Assay for Cellular $^{55}$Fe uptake and Transfer across Monolayers. Fresh supplemented DMEM was provided to the cells 1 day prior to the uptake and transfer assays. To study Fe(III) uptake and transepithelial transfer by Caco-2 cells, bacterial suspensions were traced with $^{55}$Fe (Perkin Elmer). Suspensions in volumes of 0.5 mL were placed on the apical side of Caco-2 cells, while the basolateral chamber contained 1.5 ml HBSS/HEPES.

Cells were incubated in 37° C. in a humidified atmosphere of 95% air-5% CO2. After 2 h incubation, the cells were washed four times with ice-cold wash buffer (150 mmol/L NaCl, 10 mmol/L HEPES, 1 mmol/L EDTA, pH7) and homogenized in 0.5M NaOH. $^{55}$Fe transferred to the basolateral chamber or associated with the Caco-2 lysates was measured by liquid scintillation counting. The integrity of the cell monolayers was monitored before and after the assays by measuring TEER.

Transport of $FeCl_3$ (10 µmol/l) in HBSS/HEPES with the addition of different strains of bacteria (see description of the method).

Control: as above but without bacteria.

|  | Transport % |
|---|---|
| Control | 0.06 |
| 1. *Lactobacillus plantarum* 299 | 0.58 |
| 2. *Lactobacillus plantarum* Heal 9 | 0.23 |
| 3. *Lactobacillus plantarum* 299v mutant | 0.32 |
| 4. *Lactobacillus plantarum* heal 19 | 0.69 |
| 5. *Lactobacillus plantarum* 299v | 0.38 |
| 6. *Lactobacillus reuteri* | 0.11 |

Results: The strains 1 to 5 affect the transport of Fe compared to the neat Fe solution. An increase of between 3 and 9 fold is observed. In the sample containing *Lactobacillus reuteri* an increase of the transport is seen, but not comparable with the different *Lactobacillus plantarum* strains.

Thus, the increased transport observed with the different *Lactobacillus plantarum* strain shows a similar increase in iron absorption, as shown in the earlier human studie.

The invention claimed is:

1. A method for the treatment of anemia, the method comprising orally administering to an anemic mammal in need of anemia treatment non-heme iron and a composition comprising at least one strain of viable *Lactobacillus plantarum*, in an amount of from about $1\times10^6$ to about $1\times10^{14}$ CFU, selected from the group consisting of *Lactobacillus plantarum* 299, DSM 6595, *Lactobacillus plantarum* 299v, DSM 9843, *Lactobacillus plantarum* HEAL 9, DSM 15312, *Lactobacillus plantarum* HEAL 19, DSM 15313, and *Lactobacillus plantarum* HEAL 99, DSM 15316.

2. The method according to claim 1, wherein said non-heme iron is bound with another element.

3. The method according to claim 2, wherein said composition comprises a carrier material.

4. The method according to claim 1, wherein said composition comprises a carrier material.

5. The method according to claim 4, wherein said carrier material is selected from the group consisting of oat meal gruel, lactic acid fermented foods, resistant starch, dietary fibres, carbohydrates, proteins, glycosylated proteins, and lipids.

6. The method according to claim 4, wherein said carrier material is fermented with one or more of the strains selected from the group consisting of *Lactobacillus plantarum* 299, DSM 6595, *Lactobacillus plantarum* 299v, DSM 9843, *Lactobacillus plantarum* HEAL 9, DSM 15312, *Lactobacillus plantarum* HEAL 19, DSM 15313, and *Lactobacillus plantarum* HEAL 99, DSM 15316.

7. The method according to claim 5, wherein said carrier material is fermented with one or more of the strains selected from the group consisting of *Lactobacillus plantarum* 299, DSM 6595, *Lactobacillus plantarum* 299v, DSM 9843, *Lactobacillus plantarum* HEAL 9, DSM 15312, *Lactobacillus plantarum* HEAL 19, DSM 15313, and *Lactobacillus plantarum* HEAL 99, DSM 15316.

8. The method according to claim 1, wherein said composition is selected from the group consisting of a food product, a dietary supplement, and a nutritional product.

9. The method according to claim 8, wherein said food product is selected from the group consisting of beverages, yoghurt, juices, ice cream, bread, biscuits, cereals, health bars, and spreads.

10. The method according to claim 1 wherein said at least one viable strain in the composition is present in an amount from about $1\times10^8$ to about $1\times10^{12}$ CFU.

11. The method according to claim 1 wherein said at least one viable strain in the composition is present in an amount from about $1\times10^9$ to about $1\times10^{11}$ CFU.

12. The method according to claim 1, wherein the mammal is human.

13. The method according to claim 1, wherein said non-heme iron is in food consumed by the mammal.

* * * * *